(12) United States Patent
Neumann et al.

(10) Patent No.: US 9,453,652 B2
(45) Date of Patent: Sep. 27, 2016

(54) FRAGRANCE DISPENSER

(75) Inventors: Hermann Neumann, Kenosha, WI (US); Jeffrey J. Christianson, Oak Creek, WI (US); Marcelo Lauras Ginestel, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 2356 days.

(21) Appl. No.: 12/319,606

(22) Filed: Jan. 9, 2009

(65) Prior Publication Data

US 2010/0178042 A1 Jul. 15, 2010

(51) Int. Cl.
| | |
|---|---|
| *A01G 13/06* | (2006.01) |
| *A61M 16/00* | (2006.01) |
| *F24F 11/00* | (2006.01) |
| *A01M 1/20* | (2006.01) |
| *A61L 9/03* | (2006.01) |

(52) U.S. Cl.
CPC ............ *F24F 11/00* (2013.01); *A01M 1/2077* (2013.01); *A61L 9/035* (2013.01); *A61L 2209/12* (2013.01)

(58) Field of Classification Search
None
See application file for complete search history.

(56) References Cited

U.S. PATENT DOCUMENTS

| | | |
|---|---|---|
| 2,942,090 A | 6/1960 | Diehl |
| 3,581,266 A | 5/1971 | Weyenberg |
| 4,037,082 A | 7/1977 | Tamada et al. |
| 4,549,250 A | 10/1985 | Spector |
| 4,629,604 A | 12/1986 | Spector |
| 4,714,984 A | 12/1987 | Spector |
| 4,785,642 A | 11/1988 | Chin et al. |
| 4,804,821 A | 2/1989 | Glucksman |
| 4,849,606 A | 7/1989 | Martens, III et al. |
| 4,853,517 A | 8/1989 | Bowen |
| 5,014,913 A | 5/1991 | Hoyt et al. |
| 5,111,477 A | 5/1992 | Muderlak |
| 5,136,684 A | 8/1992 | Lonker et al. |
| 5,175,791 A | 12/1992 | Muderlak et al. |
| 5,213,523 A | 5/1993 | Hygema et al. |
| 5,402,517 A | 3/1995 | Gillett et al. |
| 5,521,357 A | 5/1996 | Lock et al. |
| 5,556,192 A | 9/1996 | Wang |
| 5,574,821 A | 11/1996 | Babasade |
| 5,577,156 A | 11/1996 | Costello |

(Continued)

FOREIGN PATENT DOCUMENTS

| | | |
|---|---|---|
| EP | 1283062 | 2/2003 |
| EP | 1762253 A2 | 3/2007 |

(Continued)

OTHER PUBLICATIONS

International Search Report and Written Opinion dated Mar. 19, 2010 Appl. No. PCT/US2009/006674.

(Continued)

*Primary Examiner* — Thor Campbell

(57) ABSTRACT

A fragrance dispenser includes a housing and a plurality of heating pans disposed in the housing. Each of the plurality of heating pans includes a corresponding heating element centrally disposed therein. A controller is disposed in the housing to control the amount and temporal distribution of power distributed to each heating element independently. Prongs extend from the housing to provide power to the controller. A volatile material holder is held within the housing and includes a plurality of reservoirs adapted to align with the corresponding plurality of heating pans, wherein each of the plurality of reservoirs includes a volatile material.

10 Claims, 8 Drawing Sheets

(56) References Cited

U.S. PATENT DOCUMENTS

| | | |
|---|---|---|
| 5,647,052 A | 7/1997 | Patel |
| 5,735,460 A | 4/1998 | Eisenbraun |
| 5,788,155 A | 8/1998 | Martin et al. |
| 5,845,847 A | 12/1998 | Martin et al. |
| 5,882,256 A | 3/1999 | Shropshire |
| 5,937,140 A | 8/1999 | Leonard et al. |
| 5,945,094 A | 8/1999 | Martin et al. |
| 5,976,503 A | 11/1999 | Martin et al. |
| 6,072,165 A | 6/2000 | Feldman |
| 6,085,026 A | 7/2000 | Hammons et al. |
| 6,097,881 A | 8/2000 | DeWitt et al. |
| 6,104,866 A | 8/2000 | Dewitt |
| 6,123,935 A | 9/2000 | Wefler et al. |
| 6,141,496 A | 10/2000 | Sundberg et al. |
| 6,289,176 B1 | 9/2001 | Martter et al. |
| 6,293,474 B1 | 9/2001 | Helf et al. |
| 6,296,196 B1 | 10/2001 | Denen et al. |
| 6,341,732 B1 | 1/2002 | Martin et al. |
| 6,378,780 B1 | 4/2002 | Martens, III et al. |
| 6,382,522 B2 | 5/2002 | Tomkins et al. |
| 6,386,462 B1 | 5/2002 | Martens, III |
| 6,439,474 B2 | 8/2002 | Denen |
| 6,446,880 B1 | 9/2002 | Schram et al. |
| 6,450,419 B1 | 9/2002 | Martens, III et al. |
| D463,736 S | 10/2002 | Hern |
| D463,737 S | 10/2002 | Hern |
| D464,416 S | 10/2002 | von Dohlen et al. |
| 6,478,440 B1 | 11/2002 | Jaworski et al. |
| 6,482,863 B2 | 11/2002 | Munagavalasa et al. |
| D471,087 S | 3/2003 | McCoy et al. |
| 6,569,387 B1 | 5/2003 | Furner et al. |
| RE38,150 E | 6/2003 | Greatbatch et al. |
| 6,706,988 B1 | 3/2004 | Helf et al. |
| 6,714,725 B2 | 3/2004 | Grone et al. |
| 6,752,327 B2 | 6/2004 | Martens, III et al. |
| 6,768,865 B2 | 7/2004 | Stathakis et al. |
| 6,786,427 B2 | 9/2004 | Schram et al. |
| 6,789,741 B2 | 9/2004 | Varanasi et al. |
| 6,790,408 B2 | 9/2004 | Whitby et al. |
| 6,793,149 B2 | 9/2004 | Schramm et al. |
| 6,810,204 B2 | 10/2004 | Grone et al. |
| 6,843,430 B2 | 1/2005 | Boticki et al. |
| 6,853,801 B2 | 2/2005 | Wefler |
| 6,857,580 B2 | 2/2005 | Walter et al. |
| 6,859,615 B2 | 2/2005 | Yip et al. |
| 6,896,193 B2 | 5/2005 | Helf et al. |
| 6,917,754 B2 | 7/2005 | Pedrotti et al. |
| 6,957,012 B2 | 10/2005 | He et al. |
| 6,969,008 B2 | 11/2005 | Helf et al. |
| 6,996,335 B2 | 2/2006 | Zobele |
| 7,017,829 B2 | 3/2006 | Martens, III et al. |
| 7,046,919 B2 | 5/2006 | Shimizu et al. |
| 7,070,121 B2 | 7/2006 | Schramm et al. |
| 7,088,914 B2 | 8/2006 | Whittle et al. |
| D532,093 S | 11/2006 | Helf et al. |
| D534,640 S | 1/2007 | Helf et al. |
| 7,252,244 B2 | 8/2007 | Martens, III |
| 7,277,626 B2 | 10/2007 | Pesu et al. |
| 7,344,123 B2 | 3/2008 | Pankhurst et al. |
| 7,389,943 B2 | 6/2008 | Jaworski |
| 2002/0023639 A1 | 2/2002 | Flierl et al. |
| 2002/0048530 A1 | 4/2002 | Wohrle |
| 2004/0033171 A1 | 2/2004 | Kvietok et al. |
| 2004/0124988 A1 | 7/2004 | Leonard et al. |
| 2006/0000920 A1 | 1/2006 | Leonard |
| 2006/0175426 A1 | 8/2006 | Schramm |
| 2006/0237439 A1 | 10/2006 | Norwood |
| 2007/0075159 A1 | 4/2007 | Lin |
| 2007/0248502 A1 | 10/2007 | Adair et al. |
| 2008/0023568 A1 | 1/2008 | Weggelaar |
| 2008/0169355 A1 | 7/2008 | Pohl et al. |

FOREIGN PATENT DOCUMENTS

| | | |
|---|---|---|
| FR | 1 596 401 | 6/1970 |
| GB | 2228681 | 5/1990 |
| GB | 2275609 | 7/1994 |
| GB | 2401548 | 11/2004 |
| JP | 06-320083 | 11/1994 |
| WO | WO 02/20172 | 3/2002 |
| WO | WO 03/070287 | 8/2003 |
| WO | WO 2007/048178 | 3/2007 |

OTHER PUBLICATIONS

International Search Report and Written Opinion dated Aug. 10, 2007, Appl. No. PCT/US2007/008119.

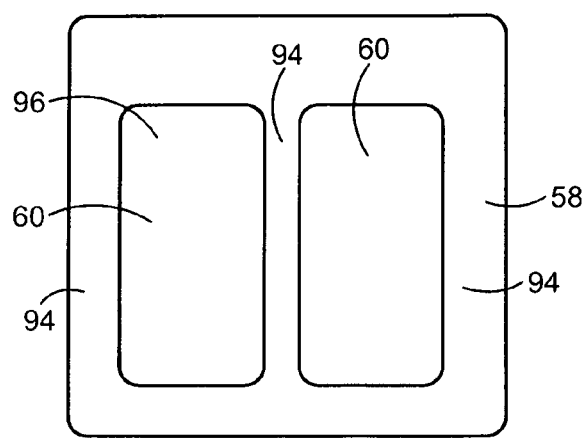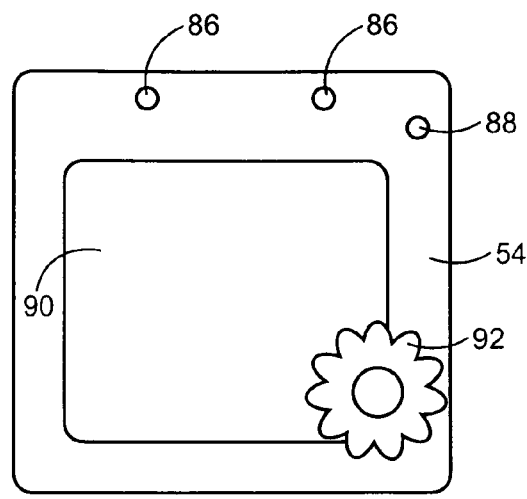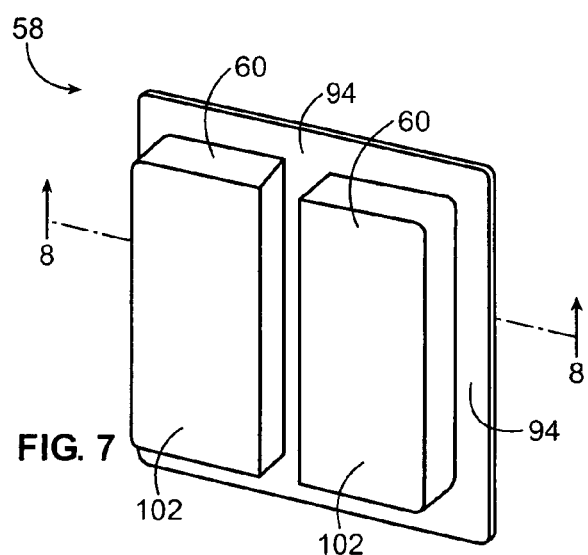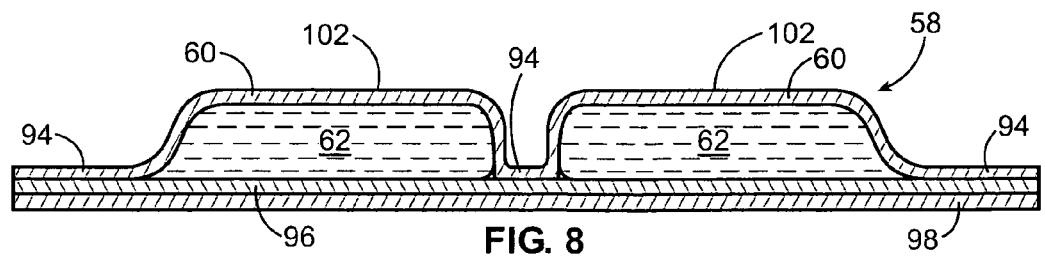

FRAGRANCE DISPENSER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to a volatile material dispensing system and, more specifically, to a plug-in volatile material dispensing system including multiple heating elements to assist in the diffusion of multiple volatile materials.

2. Description of the Background of the Invention

Volatile material dispensing systems that provide multiple sources of heat to assist in the diffusion of multiple volatile materials into the atmosphere are known in the art. For example, one dispensing system utilizes multiple porous containers, each having a reservoir filled with a fragrance laden gel. Each container is releasably inserted into a housing disposed above and spaced from an annular heating element that may be energized sequentially. An electrical plug extending from the body supplies power from a wall outlet. Heat from each heating element assists in the volatilization of a fragrance from each corresponding container. An LED corresponding to each heating element is lit up when the heating element is energized.

In another dispensing system, a container includes two independent reservoirs each filled with a gel, liquid, or solid composition. The container is releasably held within a housing and an independently controllable heating element is provided for each reservoir to increase the discharge rate of the gel composition therefrom. The dispensing system can be electronically controlled and linked to the operation of other devices.

The present disclosure contemplates a volatile material dispensing system including a multi-reservoir volatile material holder that provides for the diffusion of multiple fragrances, non-fragrancing deodorizers, insecticides, or other volatile materials as known in the art into the atmosphere. Independently controllable heating elements provide several modes of possible operation depending upon user and environmental inputs.

SUMMARY OF THE INVENTION

According to one aspect of the present invention, a fragrance dispenser comprises a housing and a plurality of heating pans disposed in the housing, wherein each of the plurality of heating pans includes a corresponding heating element centrally disposed therein. A controller is disposed in the housing to control the amount and temporal distribution of power distributed to each heating element independently. Prongs extend from the housing to provide power to the controller. A volatile material holder is held within the housing and includes a plurality of reservoirs adapted to align with the corresponding plurality of heating pans, wherein each of the plurality of reservoirs includes a volatile material.

In a different aspect of the present invention, a fragrance dispenser comprises a housing and a plurality of heating pans disposed in the housing, wherein each of the plurality of heating pans includes a corresponding heating element centrally disposed therein. A controller is disposed in the housing to control the amount and temporal distribution of power distributed to each heating element independently. Prongs extend from the housing to provide power to the controller. A volatile material holder is held within the housing and includes a plurality of reservoirs adapted to align with the corresponding plurality of heating pans, wherein each of the plurality of reservoirs includes a volatile material. A mode selector switch is disposed on the housing, wherein the amount and temporal distribution of power distributed by the controller to each heating element is at least partly determined by a setting of the mode selector switch.

In yet another aspect of the present invention, a fragrance dispenser comprises a housing and a plurality of heating pans disposed in the housing, wherein each of the plurality of heating pans includes a corresponding heating element centrally disposed therein. A controller is disposed in the housing to control the amount and temporal distribution of power distributed to each heating element independently. Prongs extend from the housing to provide power to the controller. A volatile material holder is held within the housing and includes a plurality of reservoirs adapted to align with the corresponding plurality of heating pans, wherein each of the plurality of reservoirs includes a volatile material. A mode selector switch is disposed on the housing, wherein the amount and temporal distribution of power distributed by the controller to each heating element is at least partly determined by a setting of the mode selector switch. A light source is disposed proximate to each heating pan, wherein the light source is activated with a brightness that is proportional to the amount of the power provided to each corresponding heating element.

BRIEF DESCRIPTION OF THE DRAWINGS

FIG. 5 is a front elevational view of a volatile material holder of the volatile material dispensing system of FIG. 1;

FIG. 6 is a front elevational view of a modular decorative cover of the volatile material dispensing system of FIG. 1;

FIG. 7 is a rear isometric view of the volatile material holder of FIG. 5;

FIG. 8 is a sectional view of the volatile material holder of FIGS. 5 and 7, taken generally along the line 8-8 of FIG. 7;

Other aspects and advantages of the present invention will become apparent upon consideration of the following detailed description, wherein similar structures have similar reference numerals.

DETAILED DESCRIPTION

Figure 1:
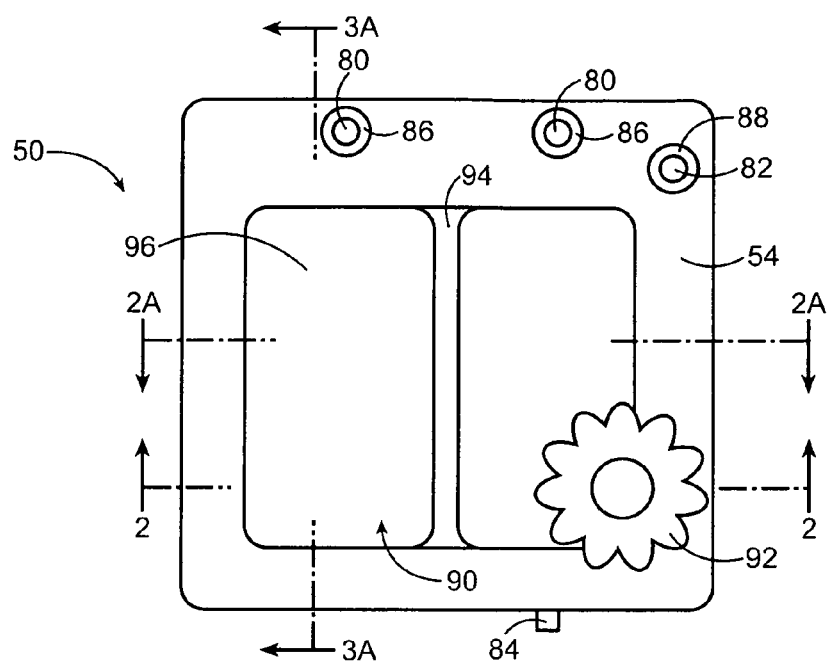
FIG. 1 is a front elevational view of an embodiment of a volatile material dispensing system.
Figure 2:
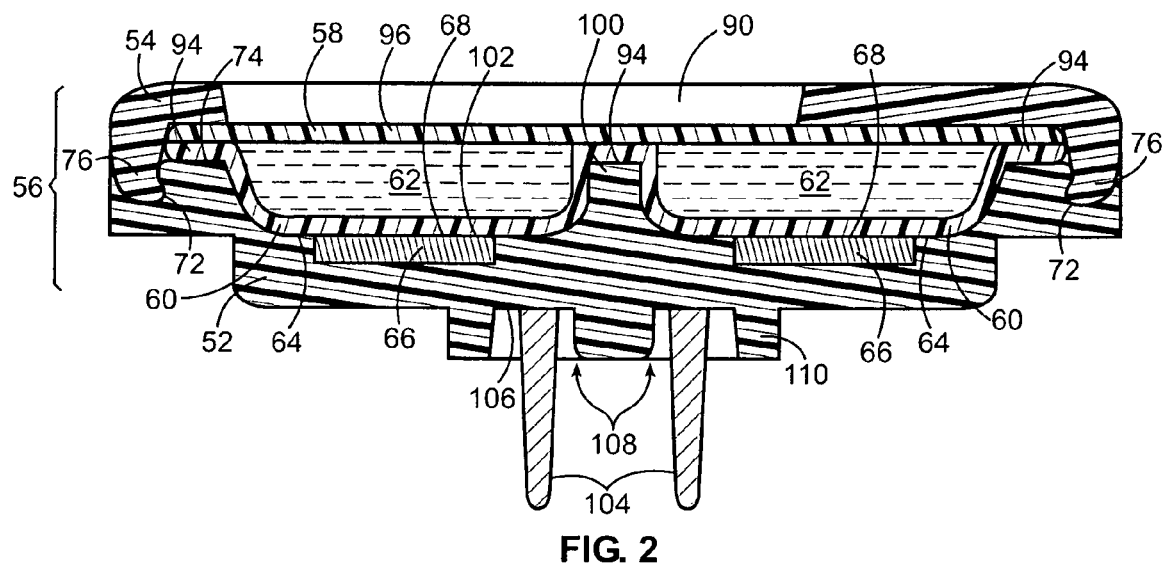
FIG. 2 is a sectional view of the volatile material dispensing system, taken generally along the line 2-2 of FIG. 1.
Figure 2A:
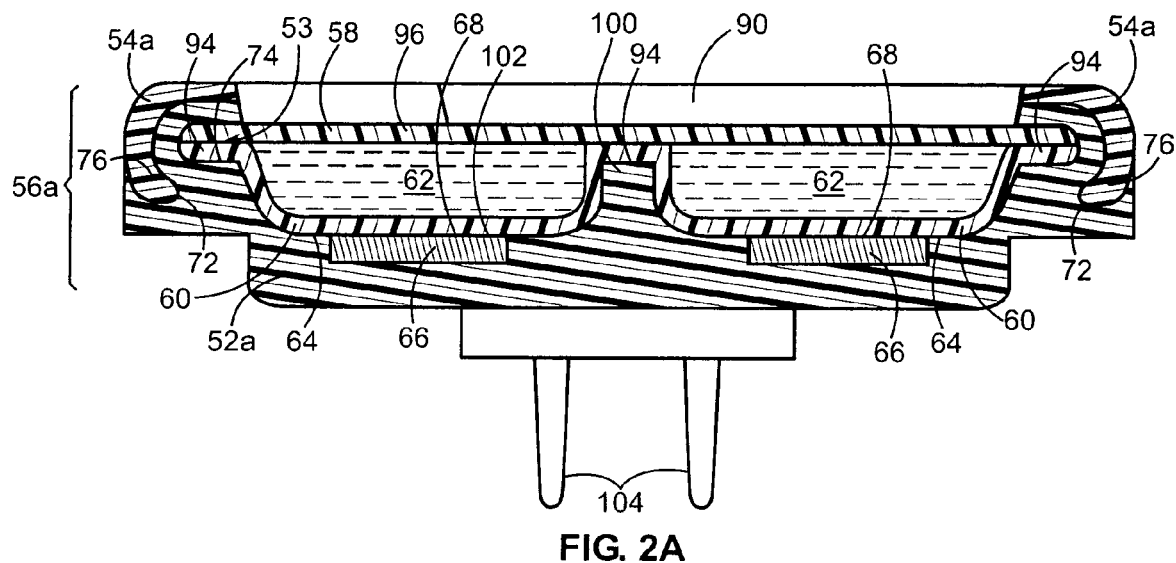
FIG. 2A is a sectional view of another embodiment of a volatile material dispensing system, taken generally along the line 2A-2A of FIG. 1.
Figure 3:
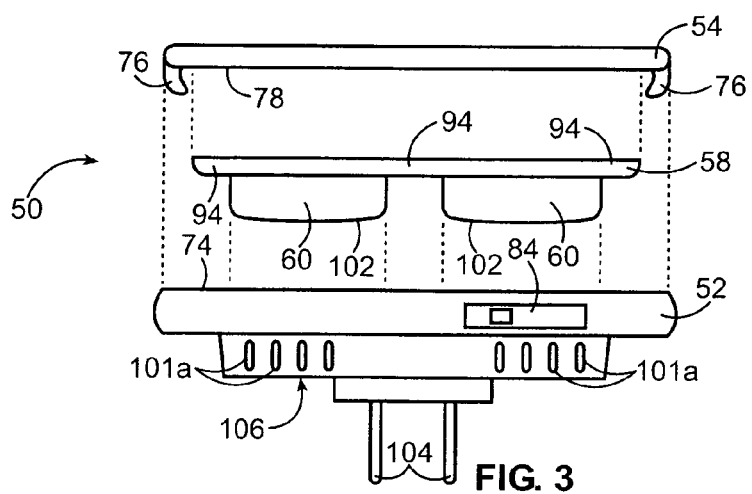
FIG. 3 is an exploded bottom view of the volatile material dispensing system of FIG. 1.
Figure 3A:
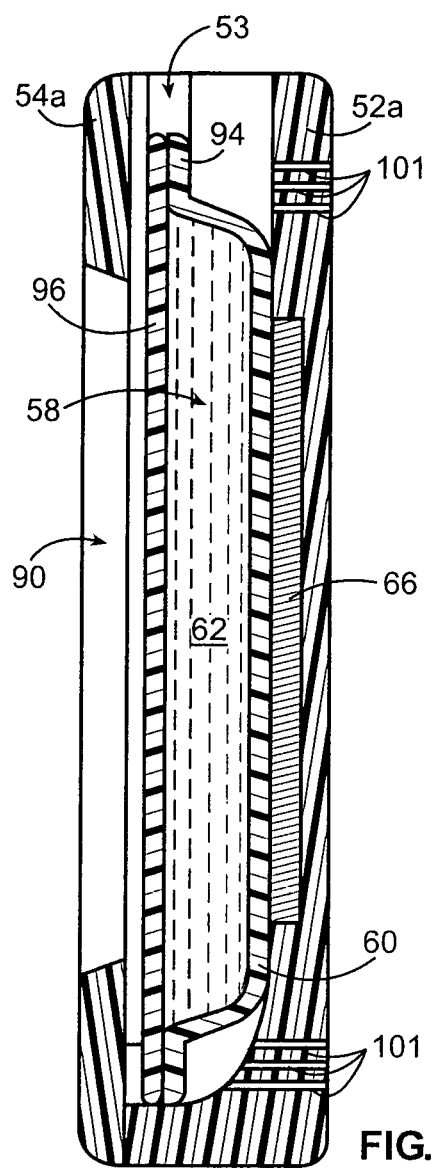
FIG. 3A is a sectional view of the volatile material dispensing system of FIG. 2A, taken generally along the line 3A-3A of FIG. 1.

Referring to FIGS. 1-6, a volatile material dispensing system 50 generally includes a base portion 52 and a modular decorative cover portion 54. In one embodiment, a housing 56 may comprise the base portion 52 and the modular decorative cover portion 54, as illustrated in FIGS. 2 and 3. In another embodiment, a housing 56a comprises a base portion 52a with a slot 53 in a top edge thereof, as illustrated in FIGS. 2A and 3A. In this embodiment, a modular decorative cover portion 54a attaches to the base 52a. A volatile material holder 58 is held within the housing 56, 56a and includes a plurality of individual reservoirs 60, for example, two, that each hold a volatile material 62 therein. The base and cover portions 52, 52a, 54, 54a may be constructed from an injection-molded plastic, such as polypropylene, or may be constructed from a different material such as glass or copolyester resin.

Figure 4:
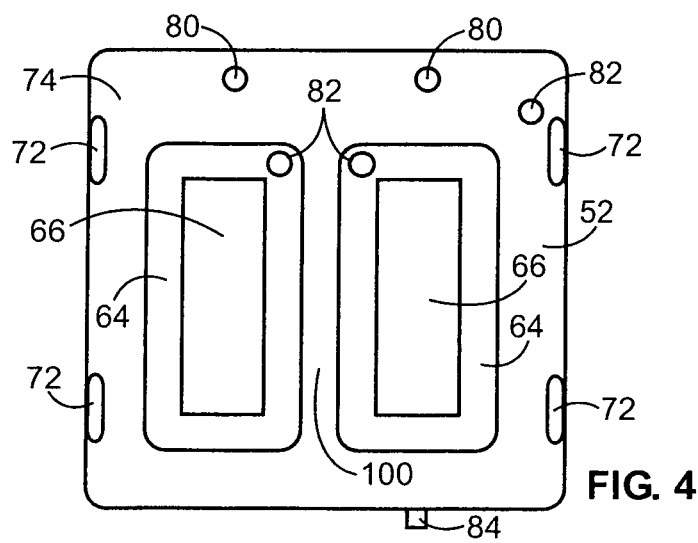
FIG. 4 is a front elevational view of a base portion of the volatile material dispensing system of FIG. 1.

Referring to FIGS. 2-4, the base portion 52, 52a includes a plurality of heating pans 64. A heating element 66 is centrally disposed within each heating pan 64 such that an exposed surface 68 of the heating element 66 is approximately flush with the surrounding surface of the heating pan 64. Each heating element 66 is independently controllable by a control circuit or controller 70 (not shown) disposed on the base portion 52, 52a. As more fully discussed hereinbelow, the controller 70 independently controls the amount and temporal distribution of power to each of the heating elements 66.

Angled recesses 72 disposed in a front surface 74 of the base portion 52, 52a receive angled teeth 76 (see FIGS. 2, 2A, and 3) extending from a rear face 78 of the cover portion 54, 54a to achieve a releasable attachment of the cover portion 54, 54a to the base portion 52, 52a. The releasable attachment may be a frictional fit or may be more of a snap fit such that the teeth 76 snap into the recesses 72. A user can separate the cover portion 54 from the base portion 52 by applying sufficient force to remove the teeth 76 from the recesses 72. In one embodiment, illustrated in FIGS. 2 and 3, after separation of the cover portion 54 from the base portion 52, a user may replace an exhausted volatile material holder 58 with a fresh volatile material holder 58 and reapply the cover portion 54 to the base portion 52. In another embodiment, illustrated in FIGS. 2A and 3A, the volatile material holder 58 is loaded into and unloaded from the base portion 52a via the slot 53 accessible from the top edge thereof. In this embodiment, the housing 56a comprises the base portion 52a by itself.

Referring to FIGS. 1 and 4, the base portion 52, 52a may include one or more light sources 80, each disposed proximate to a corresponding heating pan 64. The one or more light sources 80 are illustrated as disposed on the base portion 52, 52a and visible through one or more corresponding lighting orifices 86 when the cover portion 54, 54a is attached to the base portion 52, 52a. In other embodiments, the one or more light sources may be disposed on the cover portion 54, 54a facing away from the base portion 52, 52a, or on the base portion 52, 52a facing away from the cover portion 54, 54a to provide a back light. Each light source 80 is in electrical communication with the controller 70 and may be illuminated with a constant brightness when any amount of power to a corresponding heating element 66 is applied. Alternatively, each light source 80 may be illuminated with a brightness that is proportional to the amount of the power provided by the controller 70 to each corresponding heating element 66. In another embodiment, one or more of the light sources 80, or another light source (not shown), may be illuminated as a night light that is on whenever power is applied to the controller 70 independent of whether one of the heating elements 66 is energized. The one or more light sources 80 may be light emitting diodes (LED), incandescent bulbs, a combination of each, or another source of light or combination of other sources of light as known to one having skill in the art.

The base portion 52, 52a may also include one or more sensors 82, for example, a light sensor, a sound sensor, or a gas sensor. The one or more sensors 82 may be disposed on any region of the base portion 52, 52a, for example, within one of the heating pans 64 such that light reaching the one or more sensors 82 must pass through the corresponding individual reservoir 60 when the volatile material holder 58 is held within the housing 56, 56a. Each such sensor 82 is in electrical communication with the controller 70 and may provide an input signal to the controller 70 that the controller 70 uses to determine the amount and temporal distribution of power distributed to each heating element 66. Further, the one or more light sources 80 may have various sizes, shapes, and colors and may be configured to change color and/or intensity based on a triggering event detected by the one or more sensors 82, for example, an elapsed time period, or an environmental light level change. Each sensor 82 may provide an input signal to the controller 70 that the controller 70 uses in conjunction with the amount of the power provided to each heating element 66 to determine the brightness and/or color of each corresponding light source 80. Such controlling input from the sensor 82 may, for example, result in each light source 80 being illuminated with a greater brightness when the sensor 82 is exposed to a brighter environment, and each light source being illuminated with a lesser brightness when the sensor 82 is exposed to a more dimly lit environment. In another embodiment, one or more of the light sources 80, or another light source (not shown), may be illuminated as a night light that is on only when the sensor 82 is exposed to a dimly lit or dark environment.

A quantity of ambient light or light from one or more of the light sources 80 may be transmitted through the volatile material 62 in the reservoirs 60, and as the reservoirs 60 empty of the volatile material 62 therein, the quantity of transmitted light may increase. In another embodiment, an optical sensor may be utilized to determine the fill level of one or more of the reservoirs 60 based on the quantity of transmitted light reaching the sensor and to send an input to the controller 70 to illuminate one of the light sources 80, or another light source (not shown), to indicate that the volatile material holder 58 is empty and should be replaced. In a further example, a gas sensor sensitive to the fragrance being dispensed may be utilized to determine the fill level of one or more of the reservoirs by sending an input signal to the controller 70 in response to a sensed intensity of fragrance. In one embodiment, insertion of the volatile material holder 58 into the housing 56, 56*a* triggers the sensor 82, for example, a light sensor disposed on a region of the base portion 52, 52*a* and oriented to receive light transmitted through one of the reservoirs 60, or engages a switch (not shown) internal to the housing 56, 56*a*. The sensor 82 in response to a change in transmitted light, or the switch upon being engaged, may in conjunction with the controller 70 start timer circuitry within the controller to count down a predetermined time period, for example, 250 hours, at the conclusion of which one or more of the light sources 80, or another light source (not shown), is illuminated to indicate that the volatile material holder 58 is empty and should be replaced.

Referring to FIGS. 1, 3, 3A, and 4, the base portion 52, 52*a* may also include a mode selector switch 84, for example, in electrical communication with the controller 70 and disposed along a bottom edge as illustrated. The mode selector switch 84 may include a plurality of settings each corresponding to a mode of operation of the volatile material dispensing system 50. The particular mode of operation in effect as determined by the position of the mode selector switch 84 may at least partly determine the amount and temporal distribution of power distributed by the controller to each heating element. In fact, the mode selector switch 84 may generate a signal to the controller 70 that the controller 70 uses alone or in conjunction with a signal from each of the one or more sensors 82 to determine the amount and temporal distribution of power distributed by the controller 70 to each heating element 66 and/or to determine the brightness of each corresponding light source 80. The mode selector switch 84 is illustrated as a linear slide switch having multiple settings in FIGS. 1, 3, and 4; however, the mode selector switch may be, for example, a rotational selector switch, a set of pushbutton switches, a set of toggle switches, a bank of dip switches or any sort of selector switch or system of switches as known in the art.

Referring to FIGS. 1-3A and 6, the modular cover portion 54, 54*a* includes one or more lighting orifices 86 and one or more sensor orifices 88. Each of the lighting orifices 86 allows the underlying light source 80 to be visible from outside of the housing 56 when the cover portion 54, 54*a* is applied over the base portion 52, 52*a*. Similarly, each sensor orifice 88 provides a communicative path between each sensor 82 and the surrounding environment. The modular cover portion 54, 54*a* also includes a central opening 90 that may be partially occluded by a decorative feature 92, for example, one or more flower patterns as illustrated in FIGS. 1 and 6. The central opening 90 allows volatilized fragrance to freely escape from the volatile material holder 58 when the cover portion 54, 54*a* is applied to the base portion 52, 52*a*. The modular design of the cover portion 54, 54*a* allows a user to change the cover portion 54, 54*a*, for example, to match the décor of a room or create a look that matches the scent being dispensed.

Referring to FIGS. 1-3A, 5, 7, and 8, the volatile material holder 58 includes a plurality of independent reservoirs 60. Each of the plurality of independent reservoirs 60 is entirely surrounded by a flange 94. A non-porous permeable membrane 96 is adhered to the flange 94 to cover each of the plurality of reservoirs 60 and extends across the volatile material holder 58. As noted above, each of the independent reservoirs 60 is filled with the volatile material 62, which may comprise an active ingredient for diffusion into the surrounding atmosphere, such as a fragrance, air freshener, odor eliminator, or insect repellant insecticide. It is contemplated that any type of volatile material 62 suited for dispersal through the permeable membrane 96 may be used with the present embodiments described herein. The permeable membrane may comprise a laminate of several layers of material or may be a single layer of material. An impermeable membrane (that may also be a laminate of multiple layers) 98 is releasably adhered to the volatile material holder 58 over the permeable membrane 96.

The permeable membrane 96 is illustrated in FIGS. 1 and 5 to be transparent. However, both the permeable membrane 96 and the impermeable membrane 98 may be semi-transparent or opaque and may include colors or indicia such as text, patterns, or symbols printed or otherwise disposed thereon. The volatile material holder 58 is similar to the volatile material holders described in U.S. Pat. No. 7,441, 360, which is herein incorporated by reference in its entirety.

During a non-use state of the volatile material holder 58, the impermeable laminate 98 substantially inhibits diffusion of the volatile material 62 through the permeable membrane 96. During an in use state, the impermeable laminate 98 is removed from the volatile material holder 58. A user removes the impermeable laminate 98 by grasping an end thereof and peeling it off the volatile material holder 58. A tab, extension, or other means for grasping (not shown) may be included as an extension of the impermeable laminate 98 to aid in removal of same. The extension (not shown) is preferably provided at a corner of the impermeable laminate 98, but may extend from any portion thereof.

Removal of the impermeable laminate 98 from the volatile material holder 58 allows for the volatile material 62 to be dispersed into the atmosphere through the permeable membrane 96. In one embodiment, the permeable membrane 96 has an approximately constant permeability with temperature. In another embodiment, the permeable membrane 96 has a permeability that may vary with temperature. For example, the permeable membrane 96 may be approximately impermeable to the volatile material 62 at ambient temperature but may become substantially permeable to the volatile material 62 at a predetermined elevated temperature above ambient. This predetermined elevated temperature may be reached by heat input from the heating elements 66.

In use, as best illustrated by FIG. 2, the volatile material holder 58 is held within the base portion 52, 52*a* such that each of the independent reservoirs 60 aligns with a corresponding heating pan 64. In one embodiment, as illustrated in FIGS. 2 and 3, the volatile material holder 58 may be secured to the base portion 52 by a friction fit between the plurality of reservoirs 60 and the corresponding plurality of heating pans 64. Alternatively, the volatile material holder 58 may be secured to the base portion by an adhesive applied, for example, between the flange 94 and the base portion 52. In addition, the volatile material holder 58 may also be loosely held in the base portion 52 solely by alignment of the independent reservoirs 60 in the heating pans 64 because the secure attachment of the cover portion 54 to the base portion 52 as described hereinabove is sufficient to hold such a loosely fitting volatile material holder 58 in position for use. In another embodiment as illustrated in FIGS. 2A and 3A, the volatile material holder 58 may be secured within the housing 56a of the base 52a by a frictional fit within the slot 53, which accommodates and guides the flange 94 during installation of the volatile material holder 58 in the housing 56a. A central portion of the top edge of the base portion 52a may be recessed (not shown) to allow a portion of the flange 94 to overhang the top edge when the volatile material holder 58 is fully installed in the housing 56a. This overhang provides a user with a way to grasp the flange 94 to remove the volatile material holder 58 from the base 52a.

The surface 68 of each heating element 66 may make contact with a bottom surface 102 of each independent reservoir 60, as shown in FIGS. 2, 2A, and 3A. Alternatively, each of the heating pans 64 may be slightly deeper than each of the corresponding independent reservoirs 60 such that a small gap (not shown) remains between the surface 68 and the surface 102 when the volatile material holder 58 is held within the housing 56, 56a. A small gap may be advantageous in quickly cooling each of the heating pans 64 to minimize cross-talk after power to the corresponding heating element 66 is turned off, as described in more detail below.

Each of the independent reservoirs 60 is heated by independent application of power via the controller 70 to each of the heating elements 66 to accelerate diffusion of the volatile material 62 into the atmosphere. The heating elements 66 are thermally isolated from one another by a wall 100 therebetween. Thermal isolation between the heating elements 66 helps to minimize thermal cross-talk between the heating pans 64, which allows more precise independent control of the volatilization of the volatile material 62 from each of the independent reservoirs 60.

Figure 9:
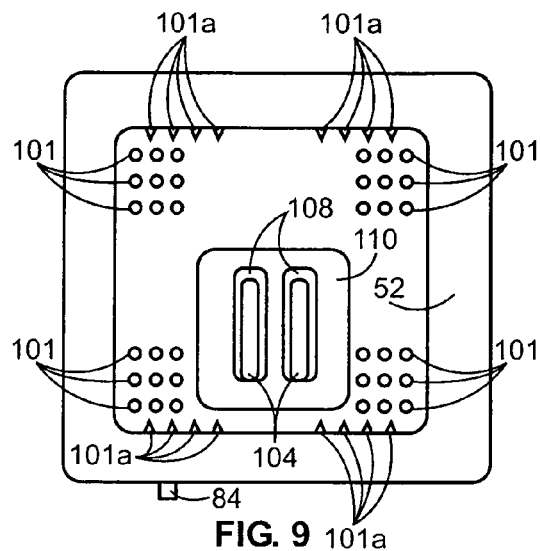
FIG. 9 is a rear elevational view of a base portion of another embodiment of a volatile material dispensing system.

To further minimize cross-talk between the heating pans 64, independent ventilation passages may be provided through the base 52, 52a for each of the heating pans 64. For example, a plurality of ventilation holes 101, as illustrated in FIGS. 3A and 9, may be disposed through the base 52, 52a. The plurality of ventilation holes 101 are positioned above and below each of the heating pans 64 when the material dispensing system 50 is oriented vertically in an in-use position. Such positioning promotes accelerated dissipation of heat from each of the de-energized heating pans 64 as a result of a convective upward flow of air between each of the heating pans 64 and the corresponding reservoir 60. The base portion 52a in FIG. 3A includes the slot 53 disposed in the top edge thereof to further provide an exit path for the convective upward flow of air. In addition, a fan (not shown) may be added to the base portion 52, 52a to force air to flow therethrough. Increased airflow through the base portion 52, 52a may enhance the convective upward flow of air or may enhance distribution of the volatile material 62 from the independent reservoirs 60 into the environment.

Alternatively, a series of ventilation slots 101a may be disposed through bottom and top edges of the base portion 52, 52a, as illustrated in FIG. 9. The plurality of ventilation slots 101a provide the same function as the plurality of ventilation holes 101 described hereinabove, and may also include a fan for enhancement of air flow through the base portion 52, 52a.

It is contemplated that another embodiment may include a single heating element (not shown) that may be moved with respect to multiple independent and thermally isolated reservoirs (not shown). This may be accomplished by moving the single heating element with respect to fixed reservoirs, moving one or more of the reservoirs with respect to a fixed single heating element, or some combination of motion of the single heating element and the reservoirs.

Referring to FIGS. 2A, 3, and 9, the base portion 52, 52a further includes electrical prongs 104 that are in electrical communication with the controller 70 and extend substantially perpendicularly from a rear surface 106 of the base portion 52, 52a. The electrical prongs 104 are adapted to be inserted into a wall outlet to provide power to the volatile material dispensing device 50. In one embodiment, illustrated in FIGS. 2 and 9, the electrical prongs 104 may be folded into grooves 108 that are defined in a protruding section 110 of the rear surface 106 such that when folded flat, the electrical prongs 104 do not extend beyond the protruding section 110. In another embodiment, an electrical cord (not shown) extends from a rear surface of the base portion 52, 52a and includes a plug for plugging into a wall outlet.

Another embodiment of a volatile material dispensing system 150, as shown in FIGS. 10-13, is substantially similar to the volatile material dispensing system described hereinabove with regard to FIGS. 1-6 except for the following differences. A base portion 152 is releasably attachable to a modular decorative cover portion 154 of a housing 156. A volatile material holder 158 is held within the housing 156 and in this embodiment includes three individual reservoirs 160 that each holds a volatile material 62 therein. Alternatively, a base portion (not shown) that is similar to the base portion 52a described hereinabove and illustrated in FIG. 3A may include a slot to define a housing that accepts the volatile material holder 158. The base portion 152 includes three heating pans 164. A heating element 166 is centrally disposed within each heating pan 164 such that an exposed surface 168 of the heating element 166 is approximately flush with the surrounding surface of the heating pan 164.

Figure 10:
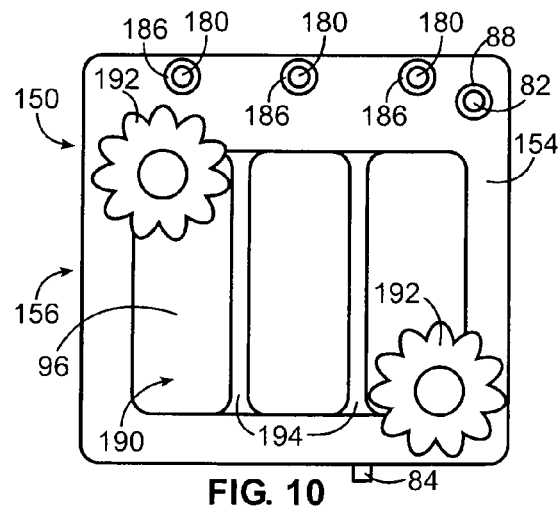
FIG. 10 is a front elevational view of a further embodiment of a volatile material dispensing system.
Figure 11:
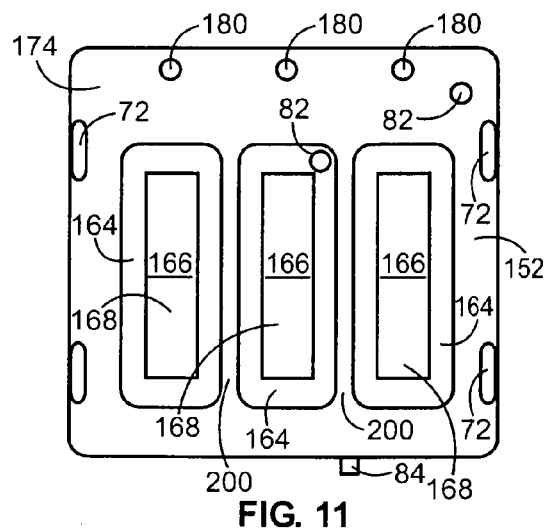
FIG. 11 is a front elevational view of a base portion of the volatile material dispensing system of FIG. 10.
Figure 12:
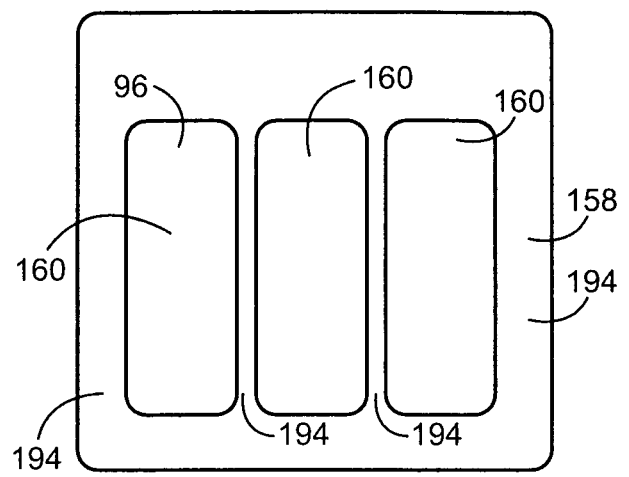
FIG. 12 is a front elevational view of a volatile material holder of the volatile material dispensing system of FIG. 10.
Figure 13:
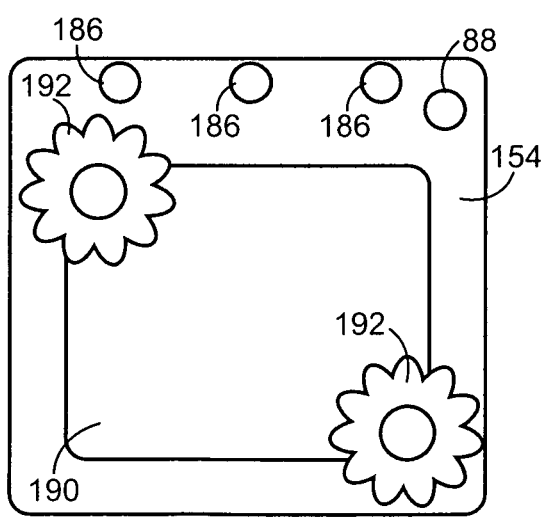
FIG. 13 is a front elevational view of a modular decorative cover of the volatile material dispensing system of FIG. 10.

In the present embodiment the base portion 152 includes three light sources 180, each disposed proximate to a corresponding heating pan 164. The modular cover portion 154 includes three lighting orifices 186 and a central opening 190 that may be partially occluded by multiple decorative features 192, for example, two flower patterns as illustrated in FIGS. 10 and 13. Referring to FIGS. 10 and 12, the volatile material holder 158 includes three independent reservoirs 160. Each of the plurality of independent reservoirs 160 is entirely surrounded by a flange 194. Further, each of the independent reservoirs 160 is heated by independent application of power via the controller 70 to each of the heating elements 166 to accelerate diffusion of the volatile material 62 into the atmosphere. The heating elements 166 are thermally isolated from one another by walls 200 therebetween.

Any of the embodiments described hereinabove may be operated in any one or all of several modes of operation. Each mode of operation is defined by a temporal relationship of application of power to the plurality of heating elements. The several modes of operation may be broadly classified into three general classes of sequential, concurrent, and mixed. It is contemplated that in addition to the possible modes of operation described hereinabove, the profile of power applied to each of the plurality of heating elements 66, 166 may be varied as a function of time. For example, the controller may distribute power to a heating element as an approximate step function, a ramp-up or ramp-down that is approximately linear with time, an approximate exponential function that asymptotically approaches a maximum or minimum value, or some other relationship. Alternatively, the controller 70 may distribute power to a heating element using a pulse width modulation scheme of repeated short bursts as is known in the art. The pulse width modulation scheme may be overlaid on any of the above-mentioned power profiles. During operation, each of the plurality of heating elements 66, 166 may have a different profile of power applied thereto. In addition, during operation within any of the above-described modes of operation, one or all of the plurality of heating elements may have profiles of power application that change from one cycle of the mode of operation to the next cycle of the mode of operation.

Figure 14:
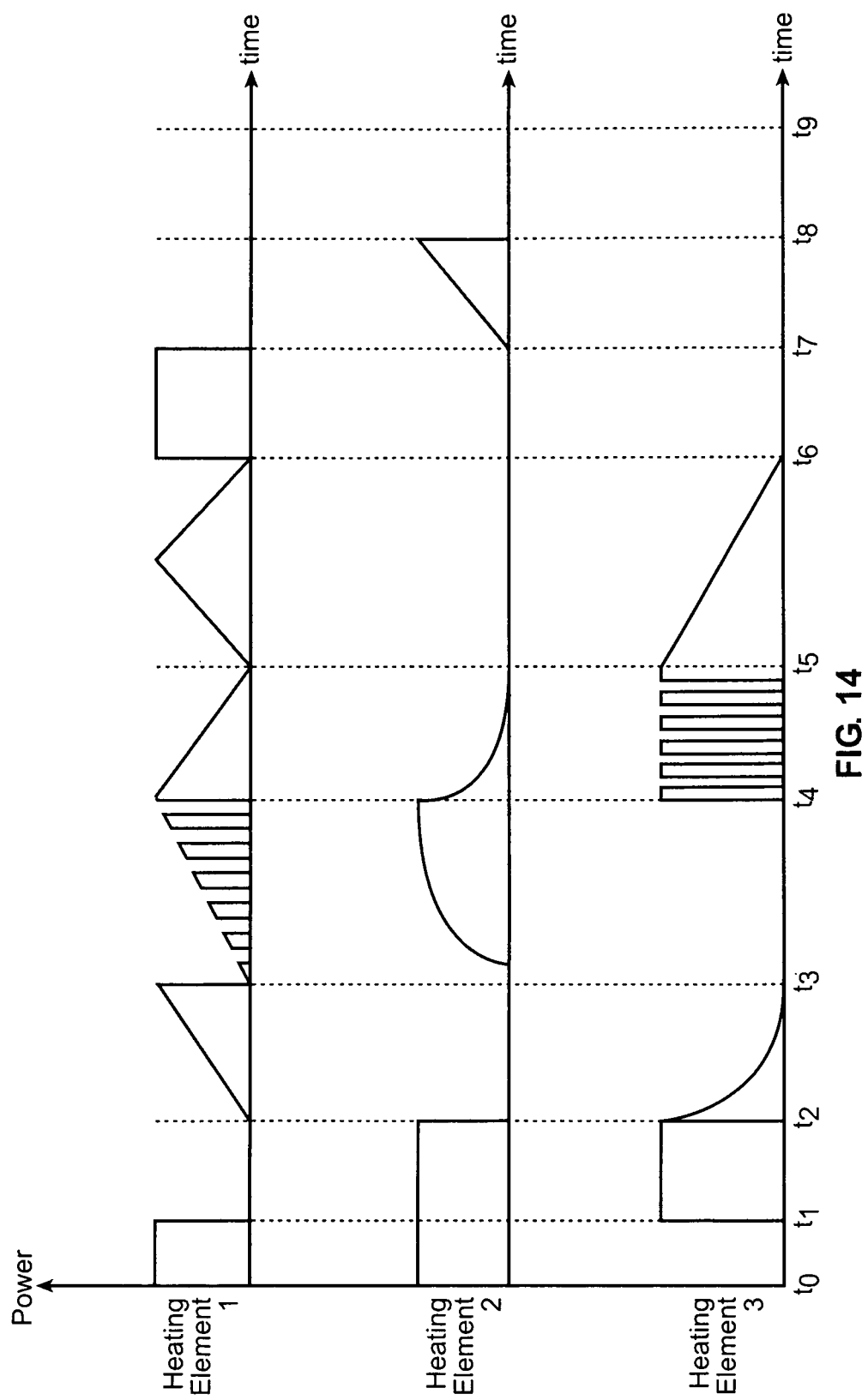
FIG. 14 is a diagram of illustrative modes of operation for a volatile material dispensing system and profiles of power applied as a function of time to each independently controlled heating element thereof.
Figure 15A:
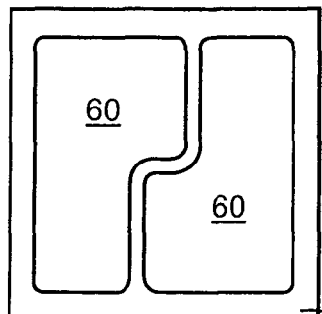
FIGS. 15A-15I depict several alternative embodiments of a volatile material holder.
Figure 15B:
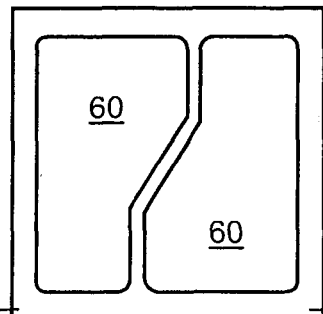
Figure 15C:
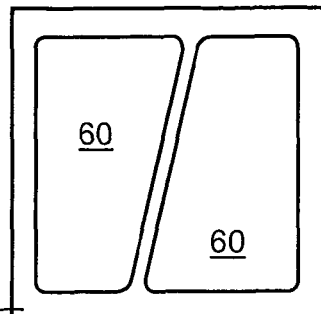
Figure 15D:
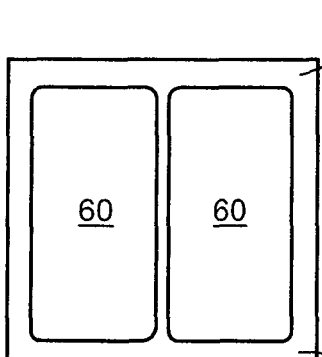
Figure 15E:
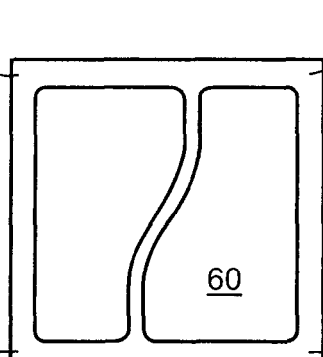
Figure 15F:
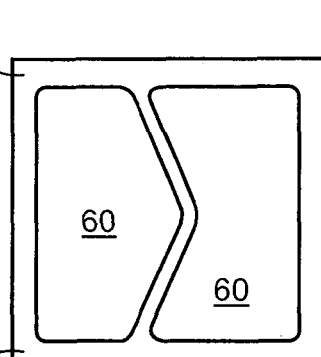
Figure 15G:
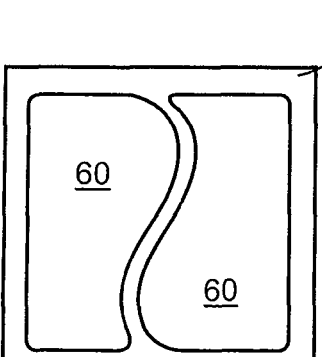
Figure 15H:
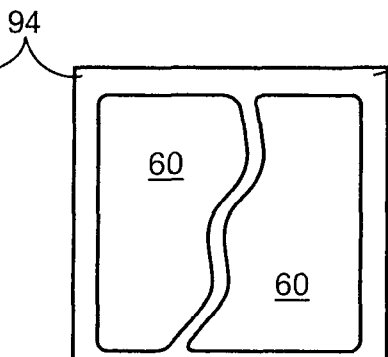
Figure 15I:
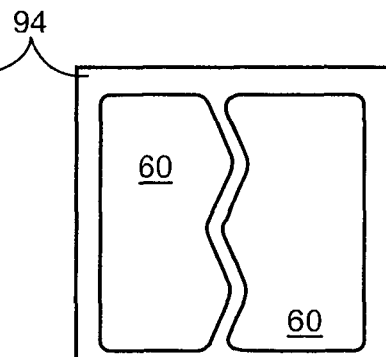

FIG. 14 illustrates each of the three general classes of the modes of operation for a volatile material dispensing system, which in the present example is illustrated by the volatile material dispensing system 150 which includes three independently controlled heating elements 166. The times $t_0$ and $t_9$ illustrated in FIG. 14 may be evenly spaced to represent equal time periods or unevenly spaced to represent unequal time periods. For example, in a sequential mode of operation, power is applied for a given time period by the controller 70 to each of the plurality of heating elements 166 in turn without overlap of the time periods. A sequential mode of operation is illustrated for the three heating elements 166 between times $t_6$ and $t_9$ in FIG. 14. Each of the time periods between $t_6$ and $t_9$ may be of equal duration or of unequal duration. In a concurrent mode of operation, power is applied concurrently for a given time period by the controller 70 to two or more of the three heating elements 166. A concurrent mode of operation is illustrated for three heating elements 166 between times $t_0$ and $t_6$ in FIG. 14. In a mixed mode of operation, both sequential and concurrent modes of operation are used in a repeating or possibly random fashion. A mixed mode of operation is illustrated for the three heating elements 166 between times $t_0$ and $t_2$ in FIG. 14. Note that two of the three heating elements 166 are energized for the entire time between $t_0$ and $t_2$; however, power is also sequentially distributed from the first heating element (top) to the third heating element (bottom) during this time.

FIG. 14 also illustrates a variety of power profiles applied to each of the three heating elements 166. A power profile approximating a step-function is illustrated for the first heating element (top) for the time period between times $t_0$ and $t_1$. Power profiles that ramp-up and/or ramp-down are also illustrated for the first heating element (top) between time periods $t_2$ and $t_6$. Power profiles that approximate a rising or falling exponential function are illustrated for the second heating element (middle) between times $t_3$ and $t_5$. Power profiles that utilize a pulse width modulation scheme are illustrated as overlaid on the ramp-up profile of the first heating element (top) between times $t_3$ and $t_4$, and overlaid on the approximate step-function profile of the third heating element (bottom) between times $t_4$ and $t_5$.

Any of the embodiments described herein may be modified to include any of the structures or methodologies disclosed in connection with different embodiments. Further, the present disclosure is not limited to volatile material dispensing systems of the type specifically shown. For example, the base portion 52, 52a and the cover portion 54, 54a may have any regular or irregular polygonal shape as desired including rectangular as illustrated hereinabove, trapezoidal, pentagonal, hexagonal, heptagonal, octagonal or may have any number of sides or a smooth continuous edge in the form of a circle, an ellipse, a snowman, a letter or word, a logo, a pattern, or any combination of curvilinear and straight edges. The cartridges may have rectangular reservoirs as illustrated hereinabove, or may have reservoirs having any polygonal shape as can be accommodated by the cartridge. For example, several possible reservoir configurations are illustrated in FIGS. 15A-15I. The multiple independent reservoirs 60 may have different capacities and may contain different volatile materials such as fragrances, non-fragrancing deodorizers, insecticides, or other volatile materials as known in the art. In addition, the multiple independent reservoirs 60 may be covered by individual permeable membranes that each has a permeability tailored to the particular material within the corresponding reservoir or tailored to a specific heat application profile for the corresponding reservoir.

INDUSTRIAL APPLICABILITY

A fragrance dispenser including multiple volatile fragrances supplied in a single volatile material holder is presented. The fragrance dispenser includes independently controllable heating elements to provide heat to each volatile fragrance. A mode selector switch and input from one or more sensors may be used to determine a mode of operation of the multiple heating elements of the fragrance dispenser. Several modes of operation are possible as well as several underlying temporal profiles for the application of power to each individual heating element.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A fragrance dispenser, comprising:
a housing;
a plurality of heating pans disposed in the housing, wherein each of the plurality of heating pans includes a corresponding heating element centrally disposed therein;
a controller disposed in the housing to control the amount and temporal distribution of power distributed to each heating element independently;
prongs that extend from the housing to provide power to the controller; and
a volatile material holder held within the housing and including a plurality of reservoirs adapted to align with the corresponding plurality of heating pans, wherein each of the plurality of reservoirs includes a volatile material.

2. The fragrance dispenser of claim 1, further comprising a mode selector switch disposed on the housing and in electrical communication with the controller, wherein the amount and temporal distribution of power distributed by the controller to each heating element is at least partly determined by a setting of the mode selector switch.

3. The fragrance dispenser of claim 2, further comprising a sensor disposed on the housing and in electrical communication with the controller, wherein a signal from the sensor is used in conjunction with the setting of the mode selector switch to determine the amount and temporal distribution of power distributed by the controller to each heating element.

4. The fragrance dispenser of claim 1, further comprising a light source disposed proximate to each heating pan, wherein the light source is activated with a brightness that is proportional to the amount of the power provided to each corresponding heating element.

5. The fragrance dispenser of claim 1, further comprising a sensor disposed on the housing and in electrical communication with the controller, wherein a signal from the sensor at least partly determines the amount and temporal distribution of power distributed by the controller to each heating element.

6. The fragrance dispenser of claim 1, wherein the housing comprises a base portion comprising the plurality of heating pans recessed in a front side thereof and a modular decorative cover portion that releasably attaches over the front side of the base portion.

7. The fragrance dispenser of claim 1, wherein the volatile material holder is held within the housing such that the plurality of reservoirs is spaced from the corresponding plurality of heating elements and ventilation passages are disposed through the housing to promote a flow of air between each of the plurality of reservoirs and the corresponding plurality of heating elements.

8. A fragrance dispenser, comprising:
a housing;
a plurality of heating pans disposed in the housing, wherein each of the plurality of heating pans includes a corresponding heating element centrally disposed therein;
a controller disposed in the housing to control the amount and temporal distribution of power distributed to each heating element independently;
prongs that extend from the housing to provide power to the controller; and
a volatile material holder held within the housing and including a plurality of reservoirs adapted to align with the corresponding plurality of heating pans, wherein each of the plurality of reservoirs includes a volatile material; and
a mode selector switch disposed on the housing, wherein the amount and temporal distribution of power distributed by the controller to each heating element is at least partly determined by a setting of the mode selector switch.

9. The fragrance dispenser of claim 8, further including a sensor disposed in the housing, wherein a signal from the sensor is used in conjunction with the setting of the mode selector switch to determine the amount and temporal distribution of power distributed by the controller to each heating element.

10. The fragrance dispenser of claim 8, further including a light source and a light sensor disposed in the housing, wherein a signal from the light sensor is used to activate the light source based on the quantity of light present in the environment of the sensor.

* * * * *